United States Patent [19]

Spranger et al.

[11] Patent Number: 4,609,728

[45] Date of Patent: Sep. 2, 1986

[54] METHOD OF TREATING A CELLULOSIC HOLLOW FIBER

[75] Inventors: Kurt Spranger, Ammerbuch-Entringen; Bernd A. W. Beck, Hechingen-Stein, both of Fed. Rep. of Germany

[73] Assignee: Gambro Dialysatoren KG, Fed. Rep. of Germany

[21] Appl. No.: 511,784

[22] Filed: Jul. 7, 1983

[30] Foreign Application Priority Data

Jun. 15, 1983 [SE] Sweden ................... 8303413

[51] Int. Cl.⁴ ............ B01D 13/04; B29D 27/04; D01F 11/02
[52] U.S. Cl. ........................... 536/56; 422/22; 422/26; 422/34; 210/500.1; 264/41
[58] Field of Search ............. 210/500.2; 264/41; 536/56; 422/22, 26, 34

[56] References Cited

U.S. PATENT DOCUMENTS

| | | | |
|---|---|---|---|
| 3,228,877 | 1/1966 | Mahon | 210/500.2 |
| 3,494,780 | 2/1970 | Skiens | 264/217 |
| 3,546,209 | 12/1970 | Lipps | 210/500 M |
| 3,864,289 | 2/1975 | Rendall | 264/41 |
| 3,917,777 | 11/1975 | Asada et al. | 264/41 |
| 4,145,295 | 3/1979 | Kutowy et al. | 264/41 |
| 4,147,622 | 4/1979 | Nussbaumer | 264/41 |
| 4,148,606 | 4/1979 | Morita et al. | 422/21 |
| 4,176,070 | 11/1979 | Sakurada et al. | 210/500 M |
| 4,240,796 | 12/1980 | Nakanishi | 427/2 |
| 4,276,173 | 6/1981 | Kell et al. | 210/500.2 |
| 4,291,470 | 9/1981 | Newman | 34/12 |
| 4,411,866 | 10/1983 | Kanno | 210/321.4 |

FOREIGN PATENT DOCUMENTS

| | | | |
|---|---|---|---|
| 70699 | 1/1970 | German Democratic Rep. | 210/500.2 |
| 1349394 | 4/1974 | United Kingdom | 210/500.2 |
| 2022117 | 12/1979 | United Kingdom . | |

OTHER PUBLICATIONS

Vol. XII Trans. Amer. Soc. Artif. Int. Organs, 1966, pp. 44-52 article "Comparison of Physical Properties and Permeability of Six Cellulose Membranes" by Wilcox et al.

Kulshrestha et al, *Cellulose Membranes for Artificial Kidney*, John Wiley & Sons, Inc, 1970, pp. 297-308.

Patent Abstract of Japan, vol. 2, No. 46, (Kokai No. 52-155219).

Patent Abstract of Japan, vol. 2, No. 31, (Kokai No. 52-125472).

*Primary Examiner*—Ronald W. Griffin
*Attorney, Agent, or Firm*—Lerner, David, Littenberg, Krumholz & Mentlik

[57] ABSTRACT

Method of treating a cellulosic hollow fiber which is being particularly adapted for use in hemodialysis or a similar extracorporeal treatment of blood.

According to the described method the hollow fiber, possibly after rinsing with an alcoholic solution or fluorinated hydrocarbons, is exposed to swelling with use of an aqueous solution prior to drying and/sterilization of the hollow fiber.

Examples of aqueous solutions can be water, water/glycerol, and water/glycerol/alcohol. Preferably said aqueous solution contains glycerol in an amount of 4–35%, such as 12–35%, preferably 16–35%.

The aqueous solution can be applied to the inside and/or the outside of the hollow fiber so as to bring about a diffusive and/or a convective transport of water and/or glycerol into the hollow fiber wall. The rate of diffusion can be increased by increasing the temperature of the aqueous solution, by increasing the contact time between the aqueous solution and the hollow fiber, or by increasing the glycerol content of the aqueous solution, and the convective transport of said substances is achieved by applying the aqueous solution under pressure.

After drying, the hollow fiber can be sterilized either by temperature or by radiation without any substantial loss of permeability characteristics.

12 Claims, No Drawings

METHOD OF TREATING A CELLULOSIC HOLLOW FIBER

TECHNICAL FIELD

A method of treating a cellulosic hollow fiber, especially for use in hemodialysis or a similar extracorporeal treatment of blood, is described.

TECHNICAL BACKGROUND

Cellulosic hollow fibers, generally known as CUPROPHAN ® hollow fibers, are extensively used in so-called artificial kidneys as a preferential means for removing middle molecule substances, such as uremic toxins, from blood of a patient suffering from a kidney disease. Usually, said hollow fibers are delivered in a dry condition, and prior to use in artificial kidneys they have to undergo treatments to restore their hydraulic permeabilities (filtration of water and diffusive permeabilities) which cause the clearance in dialysis membranes.

According to the prior art such dry cellulosic hollow fibers, as delivered, were first rinsed with either alcoholic solutions or fluorinated hydrocarbons to remove isopropyl ester which was used to maintain the dimension stability of the hollow fibers during transport, storage etc. Thereafter, the rinsed hollow fibers were treated with an alcoholic/glycerol mixture and dried.

It is general state of knowledge that a following treatment, i.e. a treatment after said rinsing, with solutions of high water content and following drying will reduce the membrane permeability (hydraulic permeabilities as defined above), and more generally it was thought that every type of wetting the cellulosic hollow fibers with following drying will reduce the above permeabilities. Additionally, it was stated that radiation sterilization of cellulosic hollow fibers will reduce the hydraulic permeability and the diffusive permeability. A similar reduction of properties is caused on dry CUPROPHAN ® membranes when sterilized by temperature, e.g. by steam sterilization.

Surprisingly, it has been found in accordance with the present invention that a cellulosic hollow fiber, possibly after a previous rinsing treatment as defined above, can be treated with an aqueous solution without any substantial loss of permeability characteristics as was expected according to the general state of knowledge. Furthermore, it was found that cellulosic hollow fibers treated according to the invention can be sterilized by radiation without loss of performances (hydraulic and diffusive permeability).

The invention will be explained in more detail in the following.

DESCRIPTION OF THE INVENTION

In accordance with the present invention there is thus provided a method of treating a cellulosic hollow fiber which is being particularly adapted for use in hemodialysis. The method is characterized by exposing the hollow fiber to swelling by means of an aqueous solution prior to drying and/or sterilization.

By swelling the hollow fiber we can thus obtain a hollow fiber which, contrary to the general statement of knowledge according to the prior art, after drying and/or sterilization has lost only a very minimal amount of hydraulic permeability characteristics.

Useful aqueous solutions according to the invention are water, water/glycerol, and water/glycerol/alcohol.

Preferred aqueous solutions contain glycerol in an amount of 4–35%, such as 12–35%, most preferably 16–35%.

According to the invention it is essential that water and/or glycerol is or are caused to come into substantially every space within the hollow fiber wall. This is achieved by diffusion and/or by convective transport of said substances.

In the diffusion process the aqueous solution is applied to the inside and/or the outside of the hollow fiber, and the rate of diffusion can be increased by increasing the temperature of the aqueous solution, by increasing the contact time between the aqueous solution and the hollow fiber, and/or by increasing the glycerol content of the aqueous solution.

In the convective-transport process the aqueous solution is applied to the inside and/or the outside of the hollow fiber under pressure so as to force said substances into the hollow fiber wall.

According to the invention it is also possible to use the combined diffusion and covective transport of said substances.

As suggested above, it has surprisingly been found that a hollow fiber which has been exposed to swelling according to the present invention can be sterilized without any substantial loss of hydraulic permeability characteristics. Especially, it has been found that a so treated hollow fiber can be properly sterilized by temperature, e.g. steam sterilization, or by radiation sterilization.

The invention will be further illustrated by means of the following examples.

EXAMPLE 1

Dependency of the performance data in relation to the glycerol content of a glycerol/water solution. Mass transport by diffusion.

GF-120-H ($8\mu$ hollow fibers) dialyzers were used in this example.

The dialyzers were rinsed on blood-side with different glycerol/water concentrations in a variation of 4–35% by weight. The solution was then kept in the blood side area for 10–60 minutes. Afterwards the solution was wasted, and the hollow fibers were dried to equilibrium conditions.

TABLE 1

| Glycerol conc. | UFR (ml/h) | Clearance in ml/min | | |
|---|---|---|---|---|
| | | $Cl^-$ | Creat. | $B_{12}$ |
| 4% | 447 | 141 | 121 | 47 |
| 8% | 554 | 133 | 116 | 44 |
| 12% | 633 | 150 | 122 | 50 |
| 16% | 667 | 177 | 142 | 58 |
| 18% | 724 | 181 | 161 | 61 |
| 20% | 758 | 175 | 154 | 58 |
| 22% | 766 | 182 | 160 | 58 |
| 35% | 770 | 175 | 150 | 60 |

Table 1 shows that in lower concentration ranges satisfying performance data were not achieved, while better values were measured beginning at a glycerol concentration of 12%, especially in convective mass transport. At higher glycerol concentrations up to 35%, significantly better clearances were realized related to diffusive mass transport. However, in the range of 16–35%, no significant performance differences were observed.

EXAMPLE 2

Dependency of the performance values in relation to transmembrane pressure at an ultrafiltration procedure with a constant glycerol concentration. Mass transport by convection.

The dialyzers were rinsed on blood-side with 18% glycerol/water concentration. At the end of the swelling process of the hollow fibers, the solution was stressed by pressure, which could be varied in a wide range until exploding pressure.

The experiment results show that by applying this method an increasing of performance data is achieved mainly in convective mass transport mechanism and in ultrafiltration-rate, respectively.

TABLE 2

| dialyzer type | transmembrane pressure | $B_{12}$ | UFR |
| --- | --- | --- | --- |
| GF 120 H (8μ) 1.2 m² | | | |
| conventional rinsing | | 55 ml/min | 645 ml/h |
| UF rinsing | 1.25 bar | 57 ml/min | 743 ml/h |
| | 1.70 bar | 66 ml/min | 840 ml/h |
| | 2.00 bar | 67 ml/min | 959 ml/h |
| GF 080 H (8μ) 0.9 m² | | | |
| conventional rinsing | | 44 ml/min | 460 ml/h |
| UF rinsing | 5.00 bar | 57 ml/min | 820 ml/h |

The above data are representative single values of investigations performed up to now.

In regard to a more effective cleaning process, the water/glycerol solution can be extended advantageously to a three-component-mixture, preferentially to a water/glycerol/alcohol solution.

EXAMPLE 3

Steam autoclaving

Sterilization method to realize a sterile, so-called dry capillary dialyzer by saturated steam.

In respect to an effective sterilization it is necessary to bring into the dialyzer sufficient humidity in form of water. This is done by rinsing and moistening the dialyzer with a two- or three-component-mixture containing water/glycerol and water/glycerol/alcohol, respectively, in adequate compositions. Having reached an equilibrium state between membrane and mixture components after the end of the water-considered swelling process, the liquid is wasted.

The application of a binary or trinary component mixture with an adequate glycerol concentration makes it possible to keep' or increase the membrane-specific glycerol content, which is of great importance for establishing the performance data.

This pre-treatment is followed by the steam autoclaving process.

The pre-treated dialyzers were packed into steam-permeable bags and put into the autoclave. The product was contacted with saturated steam and heated up to a temperature of 121° C. At this temperature a sufficient time of period was necessary to ensure the sterility of the hollow fiber dialyzers including the package. After the sterilization cycle, the dialyzers including the package were treated by adequate drying procedures to gain a dry appearance. The drying procedure has to be realized in the still closed autoclave. The performance results after this pre-treatment with following steam sterilization were comparable to the performance values achieved after conventional rinsing method and ETO-sterilization, as apparent from Table 3 below.

TABLE 3

| mean values | UFR (ml/h) | $B_{12}$ (ml/min) | Creat. (ml/min) | $Cl^-$ (ml/min) |
| --- | --- | --- | --- | --- |
| ETO-sterilization | 601 | 55 | 154 | 174 |
| steam-sterilization | 501 | 50 | 154 | 174 |

EXAMPLE 4

Gamma-sterilization

Sterilization method to realize a sterile so-called dry hollow fiber dialyzer by gamma-sterilization treatment.

The gamma-sterilization is provided by the pretreatment of the dialyzers as described in Example 3, i.e. the dialyzer was contacted and humidified with a two- or three-component mixture. For this purpose the mixture consisted advantageously of a glycerol/water solution or concerning a three-component mixture of a water/alcohol/glycerol solution of adequate membrane specific composition.

Having achieved an equilibrium state of the system membrane/component mixture after completing the swelling process with water, the liquid was wasted out of the hollow fiber dialyzer. The hollow fiber dialyzer was dried to a membrane specific condition.

In a so-called dry state the dialyzers were packed and sterilized by gamma-radiation sterilization. The radiation dosis was proportioned on the one hand according to requirements of an ensured sterility of the product and on the other hand to the effectivity of the dialyzers after sterilization.

By the help of the described pre-treatment process it was possible to increase the performance of the dialyzers after gamma-radiation in comparable values to the ETO-respectively steam-autoclaving sterilization, as apparent from Table 4 below.

TABLE 4

| Mean value | UFR (ml/h) | $B_{12}$ (ml/min) | Creat. (ml/min) | $Cl^-$ (ml/min) |
| --- | --- | --- | --- | --- |
| ETO-sterilization | 601 | 55 | 154 | 174 |
| steam-sterilization | 501 | 50 | 154 | 174 |
| gamma-radiation | 506 | 51 | 151 | 170 |

INDUSTRIAL APPLICABILITY

The method according to the present invention is particularly suitable for treating cellulosic hollow fibers for use in a so-called artificial kidney as a preferential means to removing middle molecule toxins from the blood of a patient suffering from a kidney disease.

We claim:

1. A process for making a dry, sterile dialyzer, said process comprising providing a dialyzer containing dried cuproammonium regenerated cellulose hollow fibers, treating said hollow fibers in said dialyzer with an aqueous solution including water and glycerol, then drying the hollow fibers in the dialyzer and then sterilizing the dry hollow fibers in the dialyzer by heat or radiation.

2. The process of claim 1, wherein said treating step comprises treating said hollow fibers with an aqueous solution comprising a mixture of water, glycerol and alcohol.

3. The method of claim 1, wherein said treating step comprises causing said aqueous solution to penetrate into substantially every space within the walls of said hollow fibers.

4. The process of claim 3, wherein said treating step comprises causing said aqueous solution to penetrate into said hollow fibers by diffusion.

5. The process of claim 4, wherein said treating step is carried out by applying said aqueous solution to either the interior or the exterior of said hollow fibers at increased temperatures.

6. The process of claim 4, wherein said treating step is carried out by applying said acqueous solution to either the interior or the exterior of said hollow fibers for prolonged periods of time.

7. The process of claim 4, wherein said treating step is carried out by applying said aqueous solution to either the interior or the exterior of hollow fibers under increased pressure conditions.

8. The process of claim 1, where said aqueous solution includes from about 4 to 35% glycerol.

9. The process of claim 1, wherein said aqueous solution includes from about 12 to 35% glycerol.

10. The process of claim 1, wherein said aqueous solution includes from about 16 to 35% glycerol.

11. The process of claim 1, wherein said sterilization step is carried out by the application of steam to the dry hollow fibers without bring about any substantial loss of the permeability characteristics of said hollow fibers.

12. The process of claim 1, wherein said sterilization step is carried out by the application of radiation to the dry hollow fibers without bringing about any substantial loss of the permeability characteristics of said hollow fibers.

* * * * *